US012697011B2

(12) United States Patent
Yamazaki

(10) Patent No.: US 12,697,011 B2
(45) Date of Patent: Aug. 4, 2026

(54) IMAGING DEVICE, ENDOSCOPE, AND IMAGING METHOD

(71) Applicant: OLYMPUS MEDICAL SYSTEMS CORP., Hachioji (JP)

(72) Inventor: Susumu Yamazaki, Tachikawa (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 235 days.

(21) Appl. No.: 18/750,359

(22) Filed: Jun. 21, 2024

(65) Prior Publication Data

US 2024/0423446 A1 Dec. 26, 2024

Related U.S. Application Data

(60) Provisional application No. 63/523,263, filed on Jun. 26, 2023.

(51) Int. Cl.
*A61B 1/00* (2006.01)

(52) U.S. Cl.
CPC ................................ *A61B 1/00025* (2013.01)

(58) Field of Classification Search
CPC .... A61B 1/00025; A61B 1/045; H04N 25/78; H04N 25/709; H04N 23/555
USPC .......................................................... 348/308
See application file for complete search history.

(56) References Cited

U.S. PATENT DOCUMENTS

| | | | | |
|---|---|---|---|---|
| 11,394,908 B2 * | 7/2022 | Akiyama | ............. | H04N 25/575 |
| 11,984,058 B2 * | 5/2024 | In | ......................... | G09G 3/2092 |
| 12,057,048 B2 * | 8/2024 | Pyun | .................... | G09G 3/3233 |
| 12,096,149 B2 * | 9/2024 | Park | ..................... | H04N 25/709 |
| 12,273,645 B2 * | 4/2025 | Yin | ........................ | H04N 25/78 |
| 2010/0188491 A1 * | 7/2010 | Shizukuishi | ........... | H04N 25/70 348/311 |
| 2021/0250532 A1 * | 8/2021 | Akiyama | ............... | H04N 25/65 |
| 2023/0254605 A1 * | 8/2023 | Park | ..................... | H04N 25/616 348/207.99 |
| 2023/0326388 A1 * | 10/2023 | In | ......................... | G09G 3/2092 |
| 2023/0370744 A1 * | 11/2023 | Yin | ........................ | H04N 25/78 |
| 2023/0410714 A1 * | 12/2023 | Pyun | .................... | G09G 3/2096 |

FOREIGN PATENT DOCUMENTS

JP 2017-123971 A 7/2017

* cited by examiner

*Primary Examiner* — Pritham D Prabhakher
(74) *Attorney, Agent, or Firm* — WHDA, LLP

(57) ABSTRACT

An imaging device includes two or more pixels and a voltage generation circuit. Each of the two or more pixels includes a photoelectric conversion element and a transistor. The photoelectric conversion element is configured to perform photoelectric conversion and generate an electric charge in accordance with an amount of received light. The transistor is driven by using a driving voltage. The voltage generation circuit is configured to generate the driving voltage that is lower than the power source voltage and gradually decreases.

11 Claims, 9 Drawing Sheets

IMAGING DEVICE, ENDOSCOPE, AND IMAGING METHOD

Priority is claimed on U.S. Provisional Patent Application No. 63/523,263, filed on Jun. 26, 2023, the content of which is incorporated herein by reference.

BACKGROUND OF THE INVENTION

Field of the Invention

The present invention relates to an imaging device, an endoscope, and an imaging method.

Description of Related Art

A power source voltage and a reference voltage are provided to a complementary metal-oxide-semiconductor (CMOS) image sensor (hereinafter, image sensor) in order to drive the image sensor. The image sensor includes two or more pixels. In some cases, a driving voltage between the power source voltage and the reference voltage is provided to a transistor of each of the pixels in order to improve the characteristics of the pixels.

There are two methods of generating the driving voltage between the power source voltage and the reference voltage. A first method is to generate the driving voltage outside the image sensor and input the driving voltage to the image sensor. A second method is to generate the driving voltage inside the image sensor.

In the first method, an input terminal of the driving voltage needs to be disposed in the image sensor in addition to an input terminal of the power source voltage and an input terminal of the reference voltage. According to the first method, miniaturization of the image sensor is inhibited since the number of input terminals of the image sensor increases.

In general, a power source voltage is divided by using a resistor in the second method. For example, Japanese Unexamined Patent Application, First Publication No. 2017-123971 discloses an imaging device including a circuit that generates a lower voltage than a power source voltage by using a resistor. The generated voltage is provided to a transistor in a pixel included in the imaging device.

SUMMARY OF THE INVENTION

According to a first aspect of the present invention, an imaging device is configured to operate by using a power source voltage. The imaging device includes two or more pixels and a voltage generation circuit. Each of the two or more pixels includes a photoelectric conversion element and a transistor. The photoelectric conversion element is configured to perform photoelectric conversion and generate an electric charge in accordance with an amount of received light. The transistor is driven by using a driving voltage. The voltage generation circuit is configured to generate the driving voltage that is lower than the power source voltage and gradually decreases.

According to a second aspect of the present invention, in the first aspect, the imaging device may be driven by using a clock signal. The voltage generation circuit may be configured to generate the driving voltage included in a predetermined voltage range from a first timing synchronized with the clock signal to a second timing that is synchronized with the clock signal and is different from the first timing.

According to a third aspect of the present invention, in the first aspect, the voltage generation circuit may include a capacitor and a voltage-current conversion circuit. The capacitor is configured to hold a voltage. The voltage-current conversion circuit is configured to convert the voltage held in the capacitor into a current. The voltage-current conversion circuit may be configured to start conversion into the current after the power source voltage is held in the capacitor. The voltage held in the capacitor may gradually decrease and may be output as the driving voltage while the voltage-current conversion circuit converts the voltage held in the capacitor into the current.

According to a fourth aspect of the present invention, in the first aspect, each of the two or more pixels may include a floating diffusion configured to hold the electric charge generated by the photoelectric conversion element. The transistor may be configured to transfer the electric charge generated by the photoelectric conversion element to the floating diffusion.

According to a fifth aspect of the present invention, in the first aspect, the imaging device may include two or more of the voltage generation circuits. The two or more pixels may be disposed in a matrix shape including two or more rows and two or more columns. Each of the two or more of the voltage generation circuits may be disposed so as to correspond to any one of the two or more rows.

According to a sixth aspect of the present invention, in the fifth aspect, the imaging device may include a vertical selection circuit configured to output a signal for each row of the two or more rows. Each of the two or more of the voltage generation circuits may be configured to output the driving voltage to a pixel included in the two or more pixels when the signal output from the vertical selection circuit has been received.

According to a seventh aspect of the present invention, in the fifth aspect, each of the two or more of the voltage generation circuits may include a capacitor and a voltage-current conversion circuit. The capacitor is configured to hold a voltage. The voltage-current conversion circuit is configured to convert the voltage held in the capacitor into a current. The voltage-current conversion circuit may be configured to start conversion into the current after the power source voltage is held in the capacitor. The voltage held in the capacitor may gradually decrease and may be output as the driving voltage while the voltage-current conversion circuit converts the voltage held in the capacitor into the current.

According to an eighth aspect of the present invention, in the first aspect, the imaging device may operate by using a reference voltage lower than the power source voltage. The driving voltage may be lower than the power source voltage and may be higher than the reference voltage.

According to a ninth aspect of the present invention, in the first aspect, the imaging device may operate by using a reference voltage lower than the power source voltage. The driving voltage may gradually decrease from a first voltage lower than the power source voltage to a second voltage that is lower than the first voltage and is higher than the reference voltage.

According to a tenth aspect of the present invention, an endoscope includes: a scope to be inserted into a living body; and the imaging device disposed in a distal end of the scope.

According to an eleventh aspect of the present invention, an imaging method uses an imaging device that includes two or more pixels and operates by using a power source voltage. The imaging method includes an imaging step. Each of the two or more pixels includes a photoelectric conversion element and a transistor. The photoelectric conversion element is configured to perform photoelectric conversion and generate an electric charge in accordance with an amount of received light. The transistor is driven by using a driving voltage. The imaging step includes: generating the driving voltage that is lower than the power source voltage and gradually decreases; and outputting the driving voltage to the transistor.

DETAILED DESCRIPTION OF THE INVENTION

Embodiments of the present invention will be described with reference to the drawings. Hereinafter, an example of an endoscope system including an imaging device will be described.

First Embodiment

Figure 1:
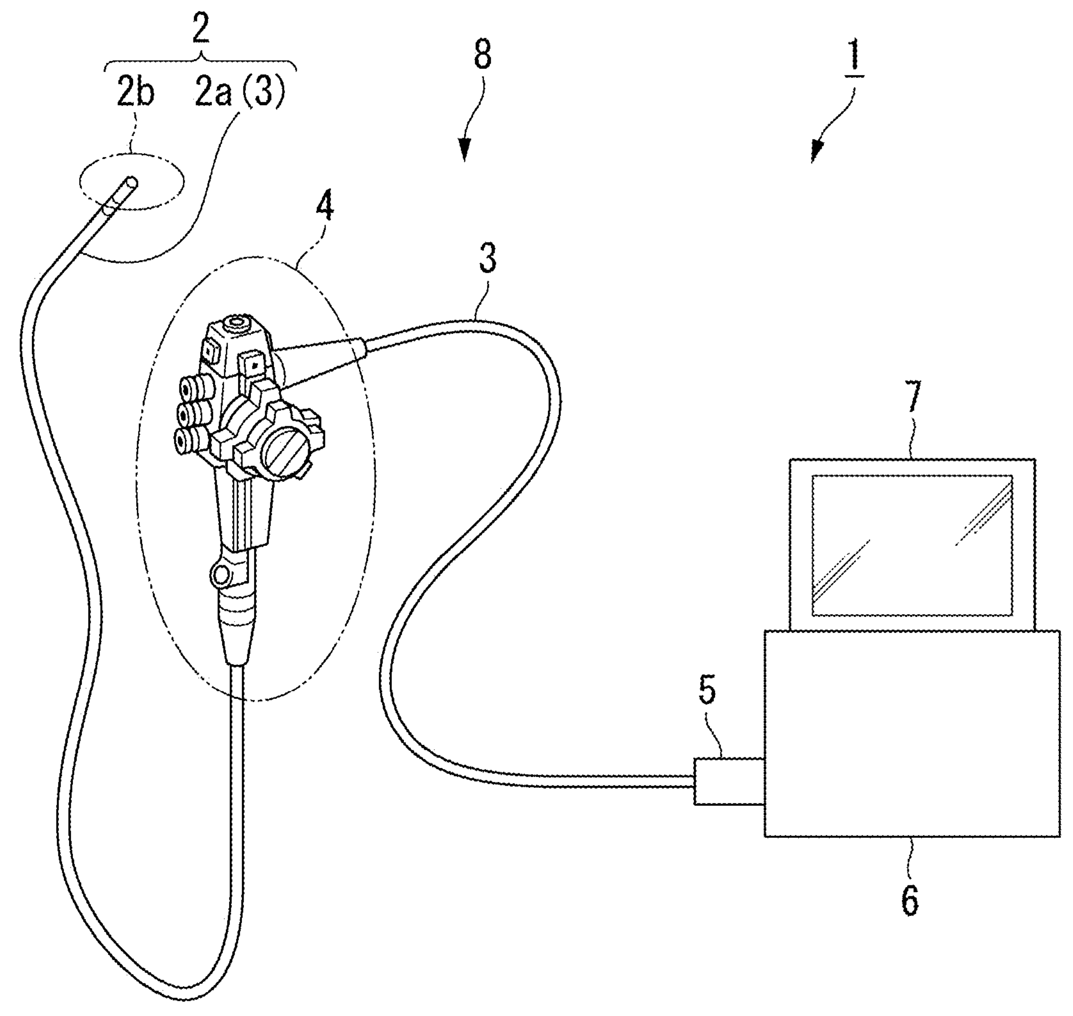
FIG. 1 is a schematic diagram showing a configuration of an endoscope system according to a first embodiment of the present invention.

FIG. 1 shows a configuration of an endoscope system 1 according to a first embodiment of the present invention. The endoscope system 1 shown in FIG. 1 includes an endoscope insertion unit 2, a transmission cable 3, an operation unit 4, a connector unit 5, a control unit 6, and a display device 7. The endoscope insertion unit 2, the transmission cable 3, the operation unit 4, and the connector unit 5 constitute a scope 8 (endoscope).

Figure 2:
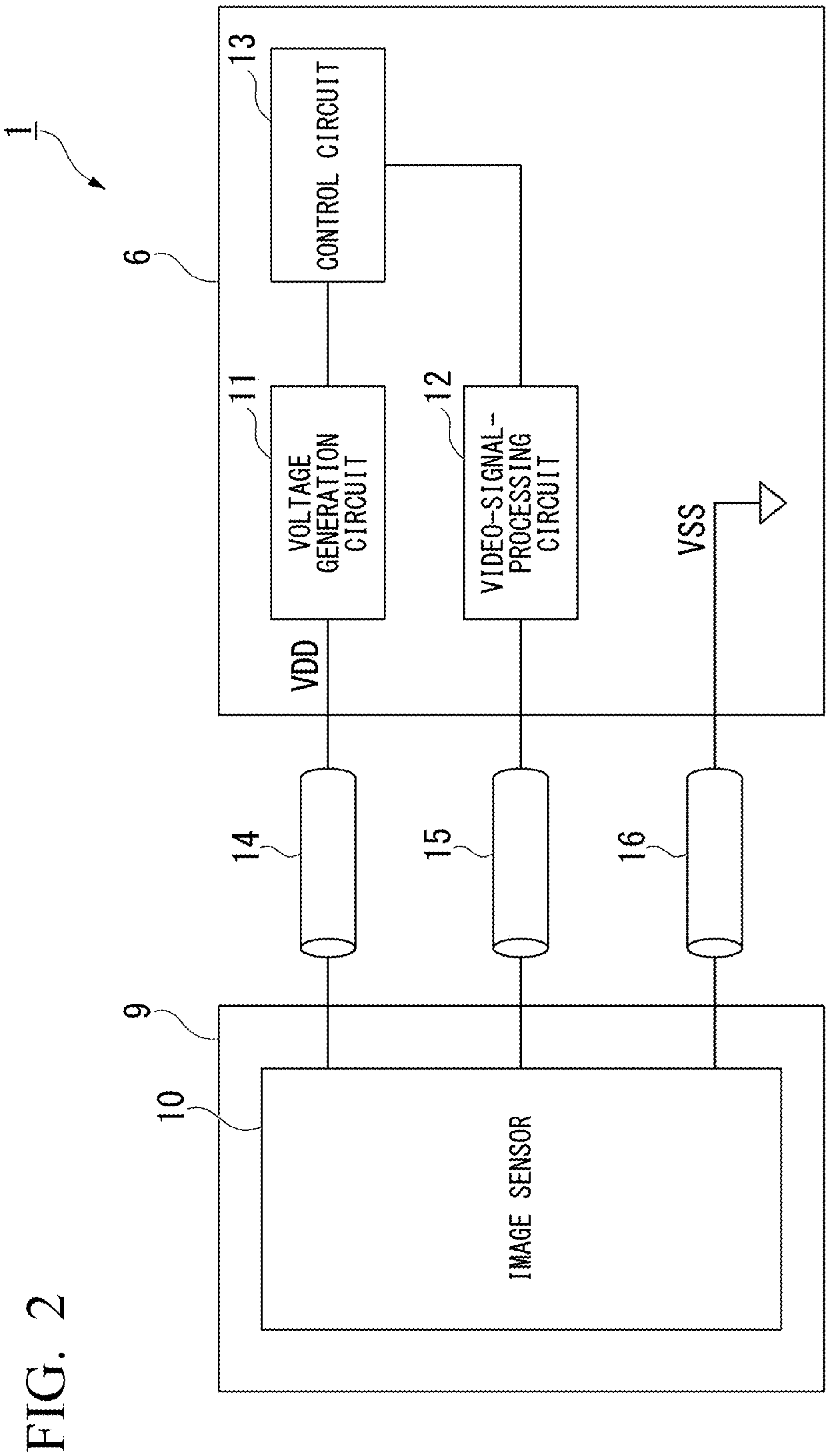
FIG. 2 is a block diagram showing a configuration of a camera unit and a control unit included in the endoscope system according to the first embodiment of the present invention.

The endoscope insertion unit 2 includes an insertion unit 2*a*. The insertion unit 2*a* is part of the transmission cable 3. The insertion unit 2*a* is to be inserted inside a living body, which is a subject. The endoscope insertion unit 2 generates a video signal by imaging the inside of the subject. The endoscope insertion unit 2 outputs the generated video signal to the control unit 6. A camera unit 9 shown in FIG. 2 is disposed in a distal end 2*b* of the insertion unit 2*a*. In the insertion unit 2*a*, the operation unit 4 is connected to the end part opposite the distal end 2*b*. The operation unit 4 receives various operations for the endoscope insertion unit 2 from a user.

The transmission cable 3 connects the camera unit 9 and the connector unit 5. The video signal generated by the camera unit 9 is output to the connector unit 5 via the transmission cable 3.

The connector unit 5 is connected to the transmission cable 3 and the control unit 6. The connector unit 5 performs predetermined processing on the video signal output from the endoscope insertion unit 2. The connector unit 5 outputs the video signal to the control unit 6.

The control unit 6 performs image processing on the video signal output from the connector unit 5. Furthermore, the control unit 6 centrally controls the entire endoscope system 1.

The display device 7 displays a video based on the video signal processed by the control unit 6. In addition, the display device 7 displays various kinds of information related to the endoscope system 1.

The endoscope system 1 includes the camera unit 9 and the control unit 6 shown in FIG. 2. FIG. 2 shows a configuration of the camera unit 9 and the control unit 6. The camera unit 9 is disposed in the distal end 2*b* of the scope 8. The operation unit 4, the connector unit 5, and the display device 7 are not shown in FIG. 2. The transmission cable 3 shown in FIG. 1 includes a power source line 14, a video signal line 15, and a reference line 16 shown in FIG. 2. The camera unit 9 and the control unit 6 are connected to each other by the power source line 14, the video signal line 15, and the reference line 16.

The endoscope system 1 includes a light source device that generates illumination light emitted to the subject. The light source device is not shown in FIG. 2.

The camera unit 9 includes an image sensor 10. The control unit 6 includes a voltage generation circuit 11, a video-signal-processing circuit 12, and a control circuit 13.

For example, the voltage generation circuit 11 is a voltage regulator. The voltage generation circuit 11 generates a power source voltage VDD that is a direct-current (DC) voltage and outputs the power source voltage VDD to the power source line 14. For example, the power source voltage VDD is 3.3 V. The power source line 14 is a signal line disposed in the transmission cable 3. The power source line 14 transfers the power source voltage VDD to the camera unit 9. The power source voltage VDD transferred by the power source line 14 is input to the image sensor 10 of the camera unit 9.

The reference line 16 is a signal line disposed in the transmission cable 3. The reference line 16 transfers a lower reference voltage VSS than the power source voltage VDD from the control unit 6 to the camera unit 9. For example, the reference voltage VSS is a ground voltage (0 V). The reference voltage VSS transferred by the reference line 16 is input to the image sensor 10 of the camera unit 9.

The image sensor 10 generates a video signal based on the power source voltage VDD and the reference voltage VSS and outputs the video signal to the video signal line 15. The video signal line 15 is a signal line disposed in the transmission cable 3. The video signal line 15 transfers the video signal to the control unit 6.

The video-signal-processing circuit 12 receives the video signal transferred by the video signal line 15. The video-signal-processing circuit 12 performs predetermined signal processing on the video signal and outputs the video signal to the display device 7. The control circuit 13 controls the operations of the voltage generation circuit 11 and the video-signal-processing circuit 12.

Figure 3:
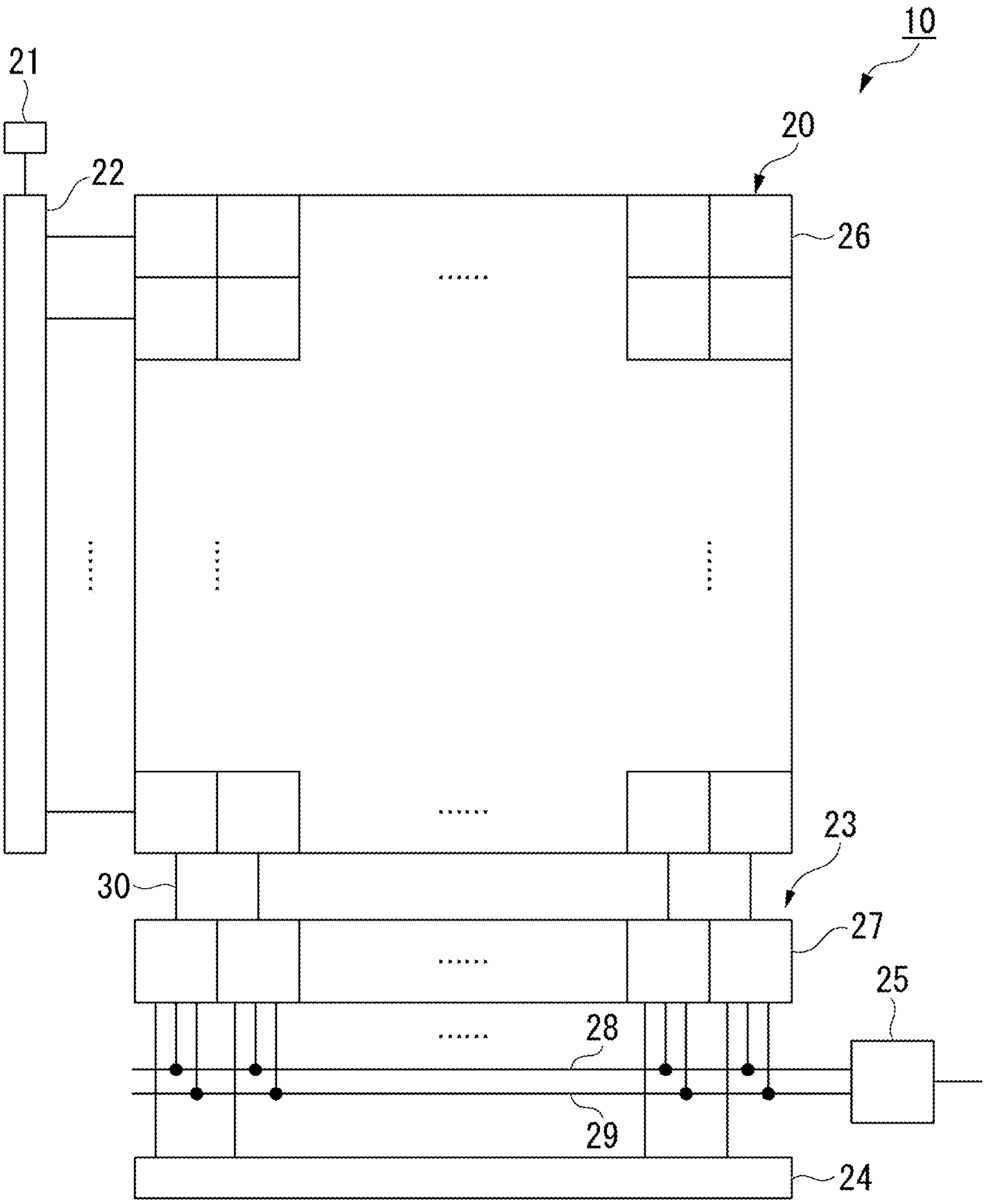
FIG. 3 is a block diagram showing a configuration of an image sensor included in the endoscope system according to the first embodiment of the present invention.

FIG. 3 shows a configuration of the image sensor 10. The image sensor 10 includes an imaging unit 20, a voltage generation circuit 21, a vertical selection circuit 22, a column circuit unit 23, a horizontal selection circuit 24, and an output unit 25. The circuits in the image sensor 10 operate in accordance with a clock signal provided from a clock generation circuit not shown in FIG. 3. The control unit 6 may include a clock generation circuit, and a clock signal generated by the clock generation circuit may be transferred to the camera unit 9.

The imaging unit 20 includes two or more pixels 26 disposed in a matrix shape. The two or more pixels 26 constitute an array having m rows and n columns. The number (m) of rows is two or more, and the number (n) of columns is two or more. The number of rows and the number of columns are not necessarily the same. Each pixel 26 outputs a first pixel signal having a reset level and a second pixel signal having a signal level.

The voltage generation circuit 21 generates a driving voltage that is higher than the reference voltage VSS and is lower than the power source voltage VDD based on the power source voltage VDD and the reference voltage VSS. The driving voltage is output to each pixel 26 via the vertical selection circuit 22.

The vertical selection circuit 22 selects pixels 26 disposed in the row direction in the array of the two or more pixels 26. The vertical selection circuit 22 controls the operations of the selected pixels 26. The vertical selection circuit 22 outputs control signals used for controlling the two or more pixels 26 for each row in the array of the two or more pixels 26.

The column circuit unit 23 includes two or more column circuits 27. Each column circuit 27 is disposed for each column in the array of the two or more pixels 26. Each column circuit 27 is connected to a vertical signal line 30 extending in the vertical direction, that is, the column direction. The vertical signal line 30 is disposed for each column in the array of the two or more pixels 26. The vertical signal line 30 is connected to pixels 26 of each column. Each column circuit 27 is electrically connected to each pixel 26 via the vertical signal line 30. Each column circuit 27 holds the first pixel signal and the second pixel signal output from each pixel 26.

Each column circuit 27 is connected to a first horizontal signal line 28 and a second horizontal signal line 29 extending in the horizontal direction, that is, the row direction. A selection pulse is output from the horizontal selection circuit 24 to each column circuit 27. The column circuit 27 selected based on the selection pulse outputs the first pixel signal to the first horizontal signal line 28 and outputs the second pixel signal to the second horizontal signal line 29.

One column circuit 27 may be disposed for two or more columns in the array of the two or more pixels 26 and may be used in the two or more columns in a time-division manner. Accordingly, the column circuit 27 has only to be disposed so as to correspond to one or more columns in the array of the two or more pixels 26.

The first horizontal signal line 28 and the second horizontal signal line 29 are connected to the output unit 25. The horizontal selection circuit 24 sequentially selects the column circuits 27 by sequentially outputting selection pulses to the column circuits 27. The first pixel signal and the second pixel signal output from the column circuit 27 selected by the horizontal selection circuit 24 are transferred to the output unit 25.

The output unit 25 generates a video signal based on the first pixel signal and the second pixel signal. For example, the video signal is the difference between the first pixel signal and the second pixel signal. The output unit 25 outputs the video signal to the video signal line 15.

Figure 4:
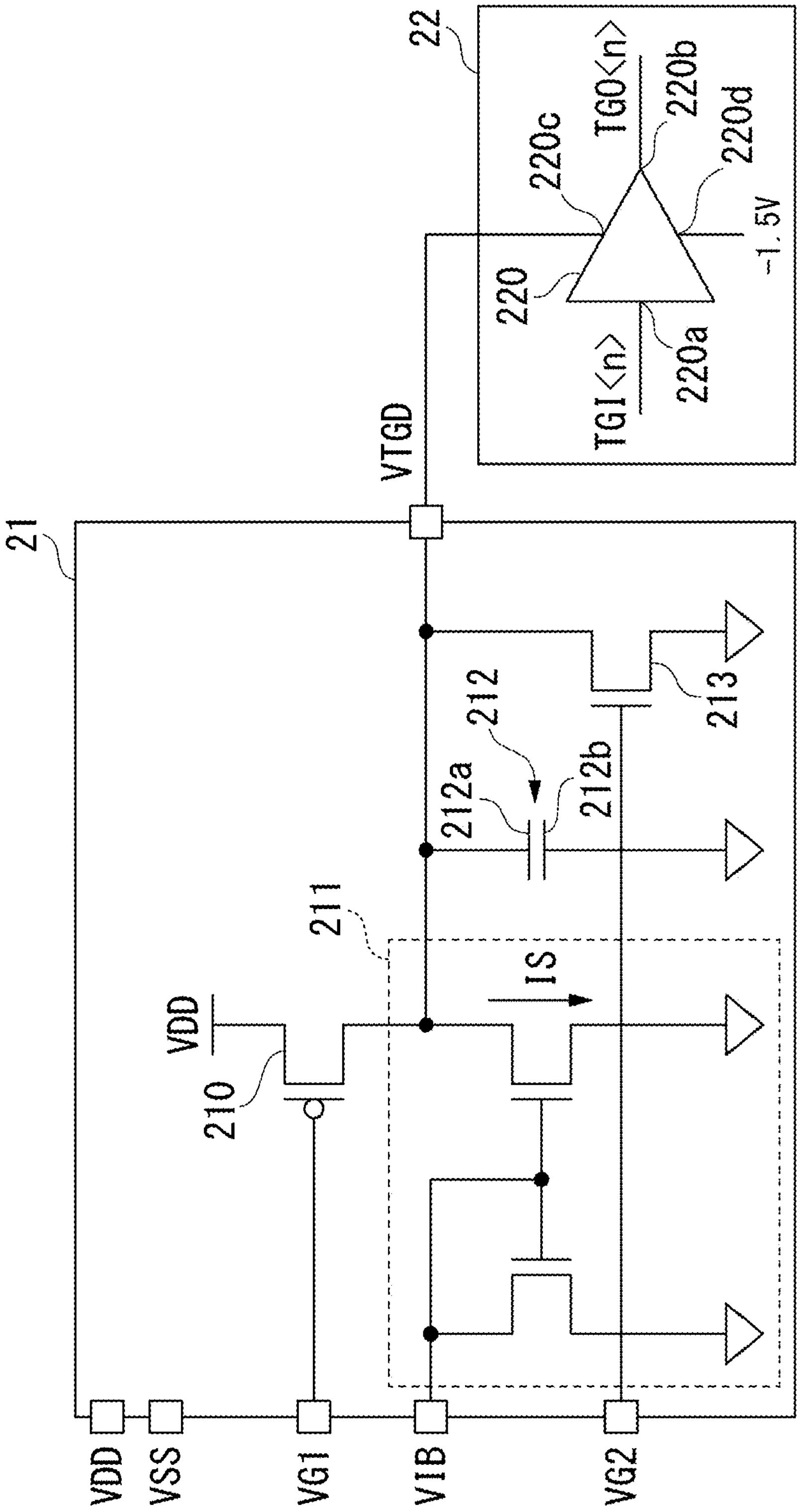
FIG. 4 is a diagram showing a configuration of a voltage generation circuit in the image sensor included in the endoscope system according to the first embodiment of the present invention.

FIG. 4 shows a configuration of the voltage generation circuit 21. The voltage generation circuit 21 includes a transistor 210, a current mirror circuit 211, a capacitor 212, and a transistor 213. The power source voltage VDD, the reference voltage VSS, a current control voltage VIB, a transistor control signal VG1, and a transistor control signal VG2 are input to the voltage generation circuit 21.

The transistors 210 and 213 are switches. The state of each of the transistors 210 and 213 becomes either an ON state or an OFF state. Each of the transistors 210 and 213 can switch between the ON state and the OFF state.

The transistor 210, the current mirror circuit 211, the capacitor 212, and the transistor 213 are connected to each other. The transistor control signal VG1 is input to the gate terminal of the transistor 210. The state of the transistor 210 is controlled in accordance with the transistor control signal VG1. When the state of the transistor 210 is the ON state, the transistor 210 outputs the power source voltage VDD.

The capacitor 212 includes a first terminal 212*a* and a second terminal 212*b*. The power source voltage VDD output from the transistor 210 is input to the first terminal 212*a*. The reference voltage VSS is input to the second terminal 212*b*. The capacitor 212 holds the power source voltage VDD. As described later, the voltage at the first terminal 212*a* gradually decreases from the power source voltage VDD. The voltage at the first terminal 212*a* is output as a driving voltage VTGD.

The current mirror circuit 211 is a current source. A fixed current IS flows through the current mirror circuit 211 in accordance with the current control voltage VIB. When the state of the transistor 210 is the OFF state, the current mirror circuit 211 converts the voltage held in the capacitor 212 into the current IS. By doing this, the current mirror circuit 211 consumes the electric charge held in the capacitor 212 as the current IS. While the current mirror circuit 211 converts the voltage held in the capacitor 212 into the current IS, the voltage at the first terminal 212*a* of the capacitor 212 gradually and smoothly decreases from the power source voltage VDD.

The transistor control signal VG2 is input to the gate terminal of the transistor 213. The state of the transistor 213 is controlled in accordance with the transistor control signal VG2. While the current mirror circuit 211 converts the voltage held in the capacitor 212 into the current IS, the state of the transistor 213 is the OFF state. When the state of the transistor 213 has been set to the ON state, the voltage at the first terminal 212*a* of the capacitor 212 is reset to the reference voltage VSS.

The vertical selection circuit 22 includes as many buffer circuits 220 as the number of rows in the array of the two or more pixels 26. The driving voltage VTGD output from the voltage generation circuit 21 is input to all the buffer circuits 220. One buffer circuit 220 is shown in FIG. 4. Each buffer circuit 220 includes an input terminal 220*a*, an output terminal 220*b*, a power source terminal 220*c*, and a power source terminal 220*d*.

An input signal TGI<n> is input to the input terminal 220*a*. The driving voltage VTGD is input to the power source terminal 220*c*, and a predetermined voltage (for example, −1.5 V) is input to the power source terminal 220*d*. The input signal TGI<n> has a high (H) voltage or a low (L) voltage. For example, the H voltage is the power source voltage VDD, and the L voltage is the reference voltage VSS. When the voltage of the input signal TGI<n> is the H voltage, an output signal TGO<n> having the driving voltage VTGD is output from the output terminal 220*b* to each pixel 26.

Figure 5:
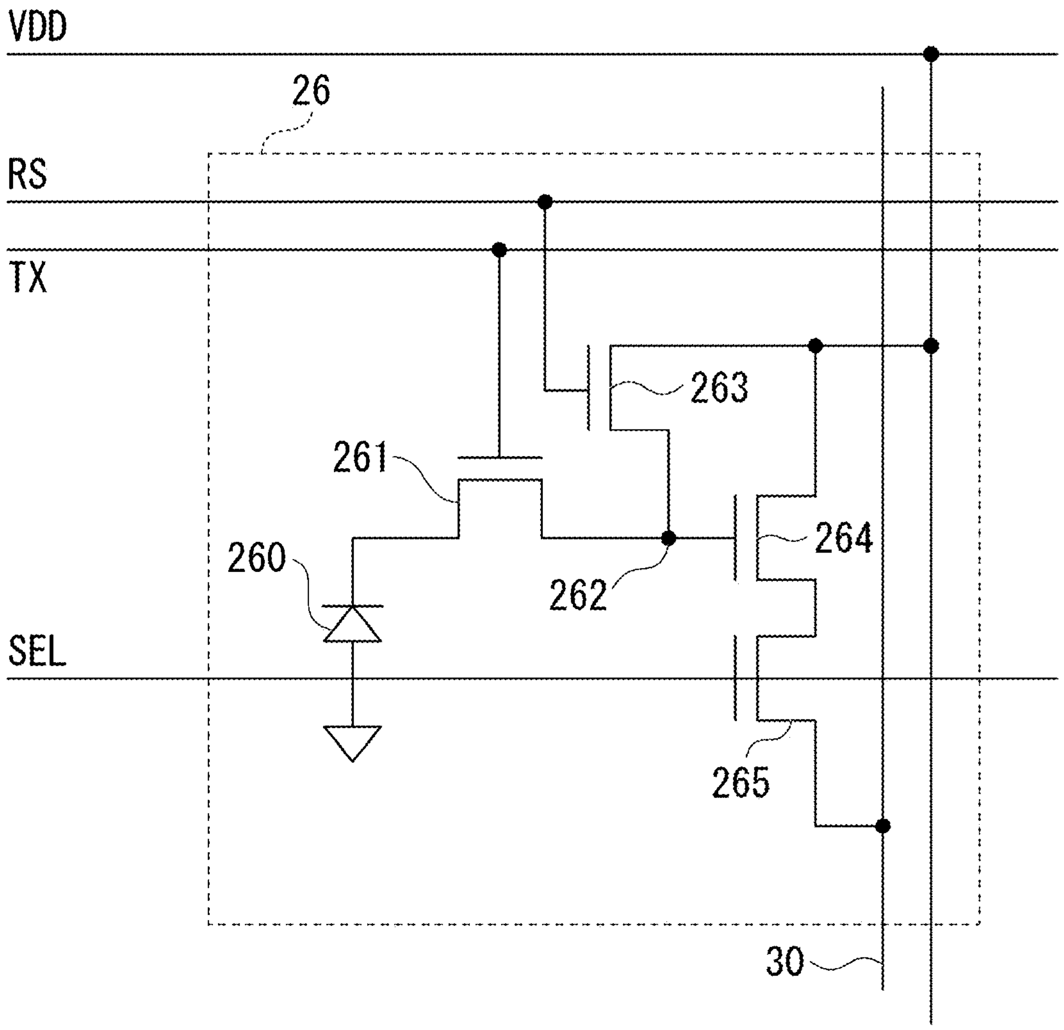
FIG. 5 is a diagram showing a configuration of a pixel in the image sensor included in the endoscope system according to the first embodiment of the present invention.

FIG. 5 shows a configuration of each pixel 26. The pixel 26 shown in FIG. 5 includes a photoelectric conversion element 260, a transfer transistor 261, a floating diffusion (FD) 262, a reset transistor 263, an amplification transistor 264, and a selection transistor 265.

The photoelectric conversion element 260 is a photodiode. The photoelectric conversion element 260 performs photoelectric conversion on light incident on the photoelectric conversion element 260 and generates an electric charge in accordance with the amount of the light. The transfer transistor 261 transfers the electric charge generated by the photoelectric conversion element 260 to the FD 262. The FD 262 holds the electric charge transferred by the transfer transistor 261.

The reset transistor 263 resets the voltage of the FD 262 to a voltage in accordance with the power source voltage VDD. By doing this, the reset transistor 263 resets the electric charge held in the FD 262. The amplification transistor 264 amplifies a signal based on the voltage of the FD 262, thus generating a pixel signal. The selection transistor 265 outputs the pixel signal to the vertical signal line 30. A first pixel signal having a reset level and a second pixel signal having a signal level are output from the pixel 26.

The vertical selection circuit 22 outputs a reset control signal RS, a transfer control signal TX, and a selection control signal SEL. The reset control signal RS is provided to the reset transistor 263. The transfer control signal TX is provided to the transfer transistor 261. The selection control signal SEL is provided to the selection transistor 265.

The transfer control signal TX corresponds to the output signal TGO<n> shown in FIG. 4. The transfer control signal TX has the driving voltage VTGD. For example, a range of the driving voltage VTGD in which the operation of the transfer transistor 261 is guaranteed is greater than or equal to 2.4 V and less than or equal to 2.6 V.

The state of each of the transfer transistor 261, the reset transistor 263, and the selection transistor 265 becomes either an ON state or an OFF state. Each transistor can switch between the ON state and the OFF state.

The state of the reset transistor 263 is controlled in accordance with the reset control signal RS. The state of the transfer transistor 261 is controlled in accordance with the transfer control signal TX. The state of the selection transistor 265 is controlled in accordance with the selection control signal SEL.

Figure 6:
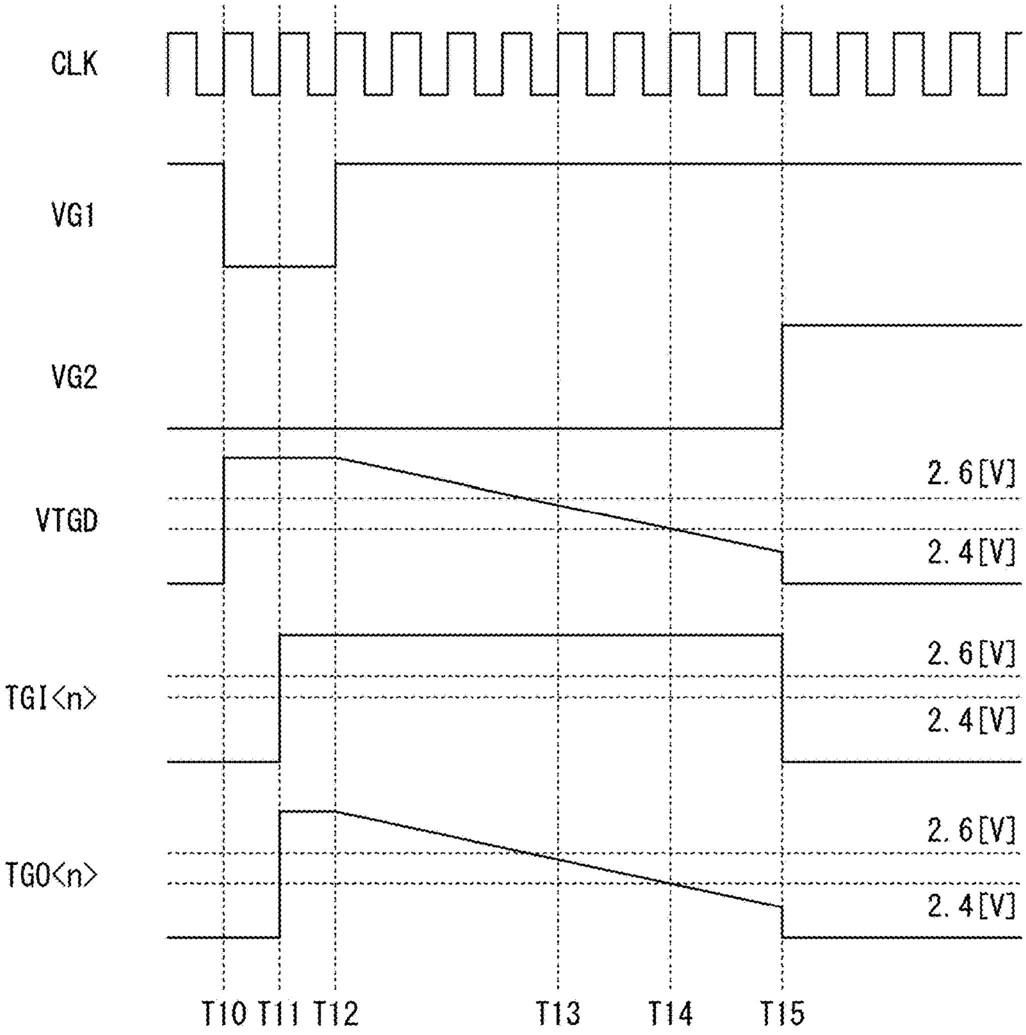
FIG. 6 is a timing chart showing waveforms of signals in the image sensor included in the endoscope system according to the first embodiment of the present invention.

FIG. 6 shows waveforms of a clock signal CLK, the transistor control signal VG1, the transistor control signal VG2, the driving voltage VTGD, the input signal TGI<n>, and the output signal TGO<n>. The horizontal direction in FIG. 6 indicates time, and the vertical direction in FIG. 6 indicates a voltage value of each signal. An operation of the voltage generation circuit 21 will be described by using FIG. 6.

The clock signal CLK is provided from the clock generation circuit to the voltage generation circuit 21. The clock signal CLK has the H voltage or the L voltage. The voltage of the clock signal CLK periodically changes between the H voltage and the L voltage. Timings of operations of circuits in the voltage generation circuit 21 are synchronized with the clock signal CLK.

Before a timing T10, the voltage of the transistor control signal VG1 is the H voltage, and the voltage of the transistor control signal VG2 is the L voltage. Therefore, the state of each of the transistor 210 and the transistor 213 is the OFF state. Before the timing T10, the driving voltage VTGD is the same as the reference voltage VSS. Before the timing T10, the voltage of each of the input signal TGI<n> and the output signal TGO<n> is the L voltage.

At the timing T10, the voltage of the transistor control signal VG1 changes from the H voltage to the L voltage. Therefore, the state of the transistor 210 changes from the OFF state to the ON state. At this time, the power source voltage VDD is output from the transistor 210 and is input to the first terminal 212*a* of the capacitor 212. The capacitor 212 holds the power source voltage VDD. The voltage generation circuit 21 outputs the same driving voltage VTGD as the power source voltage VDD.

At a timing T11 after the timing T10, the voltage of the input signal TGI<n> changes from the L voltage to the H voltage. At this time, the voltage of the output signal TGO<n> changes from the L voltage to the same voltage as the driving voltage VTGD.

At a timing T12 after the timing T11, the voltage of the transistor control signal VG1 changes from the L voltage to the H voltage. Therefore, the state of the transistor 210 changes from the ON state to the OFF state. The current mirror circuit 211 converts the voltage held in the capacitor 212 into the current IS and consumes the electric charge held in the capacitor 212 as the current IS. The voltage of the first terminal 212*a* of the capacitor 212 is output as the driving voltage VTGD. The driving voltage VTGD is shown in the following Expression (1).

$$VTGD = (Ctg/IS) * (1/t) \quad (1)$$

In Expression (1), Ctg indicates a capacitance value of the capacitor 212, and t indicates time. As shown in Expression (1), the driving voltage VTGD decreases inversely proportional to time. The speed of a change of the driving voltage VTGD can be controlled by controlling the capacitance value Ctg of the capacitor 212. The voltage of the output signal TGO<n> changes similarly to the driving voltage VTGD.

In a period from a timing T13 to a timing T14 after the timing T12, the driving voltage VTGD and the voltage of the output signal TGO<n> are greater than or equal to 2.4 V and less than or equal to 2.6 V. This period is necessary for driving the transfer transistor 261 of the pixel 26.

At a timing T15 after the timing T14, the voltage of the transistor control signal VG2 changes from the L voltage to the H voltage. Therefore, the state of the transistor 213 changes from the OFF state to the ON state. At this time, the voltage of the first terminal 212*a* of the capacitor 212 is reset to the reference voltage VSS.

The output signal TGO<n> having the driving voltage VTGD is provided to the transfer transistor 261 in a period including a period from the timing T10 to the timing T15. When the output signal TGO<n> having the driving voltage VTGD that is greater than or equal to 2.4 V and less than or equal to 2.6 V has been applied to the transfer transistor 261, the transfer transistor 261 shows predetermined performance. Before the timing T13, the operation of the transfer transistor 261 is insufficient. However, in a period from the timing T13 to the timing T14, the transfer transistor 261 can reliably transfer the electric charge generated by the photoelectric conversion element 260 to the FD 262. The output signal TGO<n> having the driving voltage VTGD may be provided to the transfer transistor 261 only in the period from the timing T13 to the timing T14.

Figure 7:
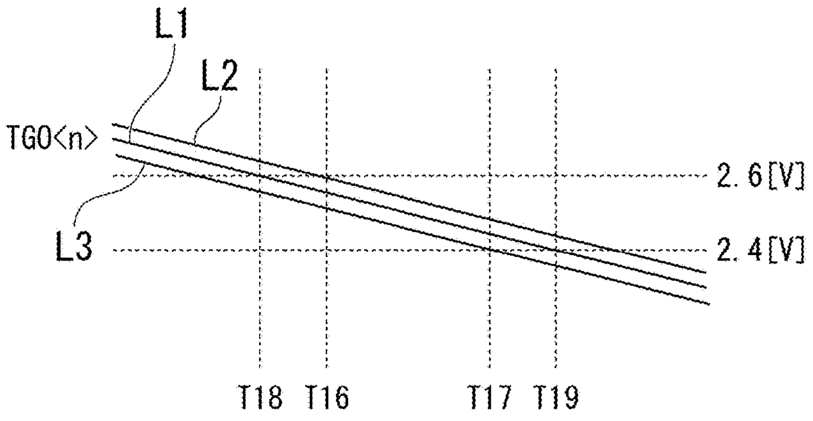
FIG. 7 is a timing chart showing a change of a voltage provided to a transfer transistor of a pixel in the first embodiment of the present invention.

A period during which the output signal TGO<n> having the driving voltage VTGD is provided to the transfer transistor 261 may be set in consideration of a change of the power source voltage VDD. As shown in FIG. 7, the output signal TGO<n> changes in accordance with a change of the power source voltage VDD. A line L1 shows a change of the output signal TGO<n> when the power source voltage VDD is a predetermined voltage (for example, 3.3 V). A line L2 shows a change of the output signal TGO<n> when the power source voltage VDD has increased. A line L3 shows a change of the output signal TGO<n> when the power source voltage VDD has decreased.

The transfer transistor 261 needs to reliably operate in a period (transistor operation period) from a timing T16 to a timing T17. At a timing T18 before the timing T16, the voltage of the output signal TGO<n> shown by the line L1 is 2.6 V. At a timing T19 after the timing T17, the voltage of the output signal TGO<n> shown by the line L1 is 2.4 V.

The voltage of the output signal TGO<n> shown by the line L2 is higher than 2.6 V from the timing T18 to the timing T16. The voltage of the output signal TGO<n> shown by the line L3 is lower than 2.4 V from the timing T17 to the timing T19. When the power source voltage VDD has increased or decreased, the operation of the transfer transistor 261 is insufficient in a period from the timing T18 to the timing T16 or in a period from the timing T17 to the timing T19.

The voltage of the output signal TGO<n> shown by the line L2 is greater than or equal to 2.4 V and less than or equal to 2.6 V in the transistor operation period. Similarly, the voltage of the output signal TGO<n> shown by the line L3 is greater than or equal to 2.4 V and less than or equal to 2.6 V in the transistor operation period. In other words, even when the power source voltage VDD changes, the voltage of the output signal TGO<n> in the transistor operation period is greater than or equal to 2.4 V and less than or equal to 2.6 V. Therefore, the transfer transistor 261 can reliably operate in the transistor operation period.

When the power source voltage VDD is a predetermined voltage, the voltage generation circuit 21 outputs the driving voltage VTGD that is greater than or equal to 2.4 V and less than or equal to 2.6 V in a period that includes the transistor operation period and is longer than the transistor operation period. By doing this, the voltage generation circuit 21 can generate the driving voltage VTGD of a predetermined range in the transistor operation period even when the power source voltage VDD changes.

In the above-described example, the output signal TGO<n> having the driving voltage VTGD is provided to the transfer transistor 261. In a case in which the reset transistor 263 or the selection transistor 265 is driven by using a voltage between the reference voltage VSS and the power source voltage VDD, the output signal TGO<n> having a voltage generated by using a similar method to that of generating the driving voltage VTGD may be provided to the reset transistor 263 or the selection transistor 265.

In the first embodiment, the image sensor 10 (imaging device) operates by using the power source voltage VDD. The photoelectric conversion element 260 performs photoelectric conversion and generates an electric charge in accordance with the amount of received light. The transfer transistor 261 is driven by using the driving voltage VTGD. The voltage generation circuit 21 generates the driving voltage VTGD that is lower than the power source voltage VDD and gradually decreases.

An imaging method of each aspect of the present invention includes an imaging step. The imaging step includes a first step and a second step. The voltage generation circuit 21 generates the driving voltage VTGD that is lower than the power source voltage VDD and gradually decreases in the first step (from the timing T12 to the timing T15). The voltage generation circuit 21 outputs the driving voltage VTGD to the transfer transistor 261 in the second step (from the timing T12 to the timing T15).

Each aspect of the present invention may include the following modified example. The image sensor 10 (imaging device) is driven by using the clock signal CLK. The voltage generation circuit 21 generates the driving voltage VTGD included in a predetermined voltage range (greater than or equal to 2.4 V and less than or equal to 2.6 V) from a first timing (T13) synchronized with the clock signal CLK to a second timing (T14) that is synchronized with the clock signal CLK and is different from the first timing.

Each aspect of the present invention may include the following modified example. The voltage generation circuit 21 includes the capacitor 212 and the current mirror circuit 211 (voltage-current conversion circuit). The capacitor 212 holds a voltage. The current mirror circuit 211 converts the voltage held in the capacitor 212 into the current IS. After the power source voltage VDD is held in the capacitor 212, the current mirror circuit 211 starts conversion into the current IS. While the current mirror circuit 211 converts the voltage held in the capacitor 212 into the current IS, the voltage held in the capacitor 212 gradually decreases and is output as the driving voltage VTGD.

Each aspect of the present invention may include the following modified example. The FD 262 holds the electric charge generated by the photoelectric conversion element 260. The transfer transistor 261 transfers the electric charge generated by the photoelectric conversion element 260 to the FD 262.

Each aspect of the present invention may include the following modified example. The image sensor 10 (imaging device) operates by using the reference voltage VSS lower than the power source voltage VDD. The driving voltage VTGD is lower than the power source voltage VDD and is higher than the reference voltage VSS.

Each aspect of the present invention may include the following modified example. The driving voltage VTGD gradually decreases from a first voltage (for example, 2.6 V) lower than the power source voltage VDD to a second voltage (for example, 2.4 V) that is lower than the first voltage and is higher than the reference voltage VSS.

Each aspect of the present invention may include the following modified example. An endoscope includes both the scope 8 to be inserted inside a living body and the image sensor 10. The image sensor 10 is disposed in the distal end 2*b* of the scope 8.

As shown in FIG. 7, the voltage generation circuit 21 can generate the driving voltage VTGD of a predetermined range in the transistor operation period even when the power source voltage VDD changes. Therefore, the voltage generation circuit 21 can generate the stable driving voltage VTGD.

In a voltage generation circuit that generates a fixed voltage, many transistors are required in order to generate the voltage with high accuracy. Since the voltage generation circuit 21 generates the driving voltage VTGD that gradually decreases, the number of necessary transistors for the voltage generation circuit 21 decreases. Therefore, the image sensor 10 can be miniaturized.

The voltage generation circuit 21 generates the driving voltage VTGD that is greater than or equal to 2.4 V and less than or equal to 2.6 V from the timing T13 to the timing T14. The timing T13 and the timing T14 are synchronized with the clock signal CLK. The voltage generation circuit 21 can generate the driving voltage VTGD of a predetermined range in a period determined in accordance with the clock signal CLK.

Second Embodiment

Figure 8:
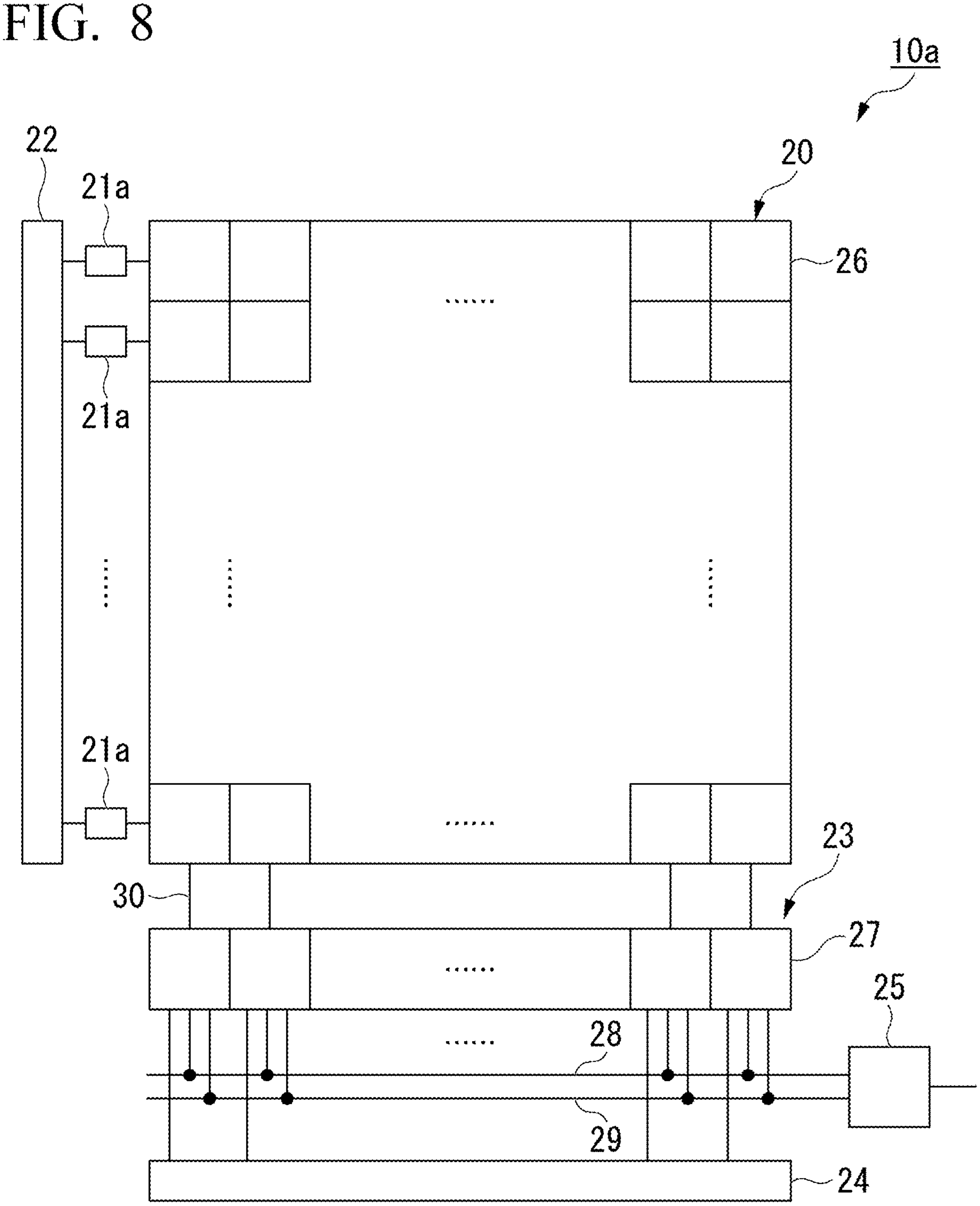
FIG. 8 is a block diagram showing a configuration of an image sensor included in an endoscope system according to a second embodiment of the present invention.

A second embodiment of the present invention will be described. The image sensor 10 shown in FIG. 3 is changed to an image sensor 10*a* shown in FIG. 8. FIG. 8 shows a configuration of the image sensor 10*a*. The same parts as those shown in FIG. 3 will not be described.

The image sensor 10*a* includes an imaging unit 20, two or more voltage generation circuits 21*a*, a vertical selection circuit 22, a column circuit unit 23, a horizontal selection circuit 24, and an output unit 25. The two or more voltage generation circuits 21*a* are disposed between the vertical selection circuit 22 and the imaging unit 20. Each voltage generation circuit 21*a* is disposed so as to correspond to any one of two or more rows.

In the image sensor 10 shown in FIG. 3, one voltage generation circuit 21 is disposed. The driving voltage VTGD output from the voltage generation circuit 21 is input to the buffer circuit 220 disposed for each row of the two or more rows. Since the distance between the voltage generation circuit 21 and the buffer circuit 220 is different between the two or more rows, a delay of the driving voltage VTGD may occur in accordance with a row position.

In the image sensor 10*a* shown in FIG. 8, each voltage generation circuit 21*a* is disposed for each row of the two or more rows. Therefore, the distance between each voltage generation circuit 21*a* and the buffer circuit 220 is fixed, and a delay of the driving voltage VTGD does not occur in accordance with a row position.

Figure 9:
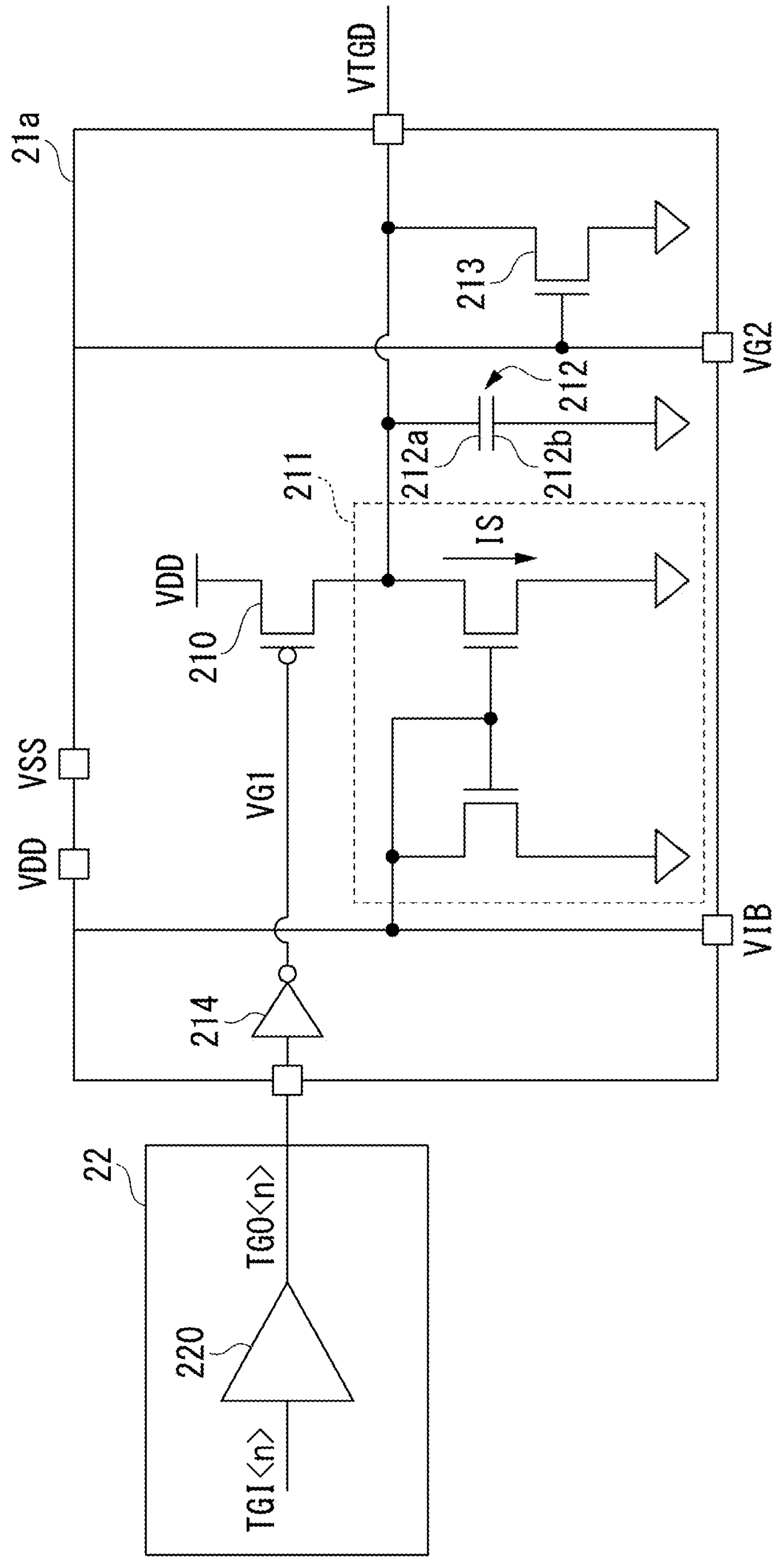
FIG. 9 is a diagram showing a configuration of a voltage generation circuit in the image sensor included in the endoscope system according to the second embodiment of the present invention.

FIG. 9 shows a configuration of the voltage generation circuit 21*a*. The same parts as those shown in FIG. 4 will not be described. The voltage generation circuit 21*a* includes a transistor 210, a current mirror circuit 211, a capacitor 212, a transistor 213, and an inverter 214. The power source voltage VDD, the reference voltage VSS, the current control voltage VIB, and the transistor control signal VG2 are input to the voltage generation circuit 21*a*.

The vertical selection circuit 22 includes as many buffer circuits 220 as the number of rows in the array of the two or more pixels 26 as in the first embodiment. One buffer circuit 220 is shown in FIG. 9. The input signal TGI<n> is input to the buffer circuit 220, and the output signal TGO<n> is output from the buffer circuit 220.

The output signal TGO<n> is input to the inverter 214. The inverter 214 inverts the voltage of the output signal TGO<n>, thus generating the transistor control signal VG1. The transistor control signal VG1 is output to the gate terminal of the transistor 210.

The voltage of the first terminal 212*a* of the capacitor 212 is output as the driving voltage VTGD as in the first embodiment. The driving voltage VTGD is provided to the transfer transistor 261 of each pixel 26.

Figure 10:
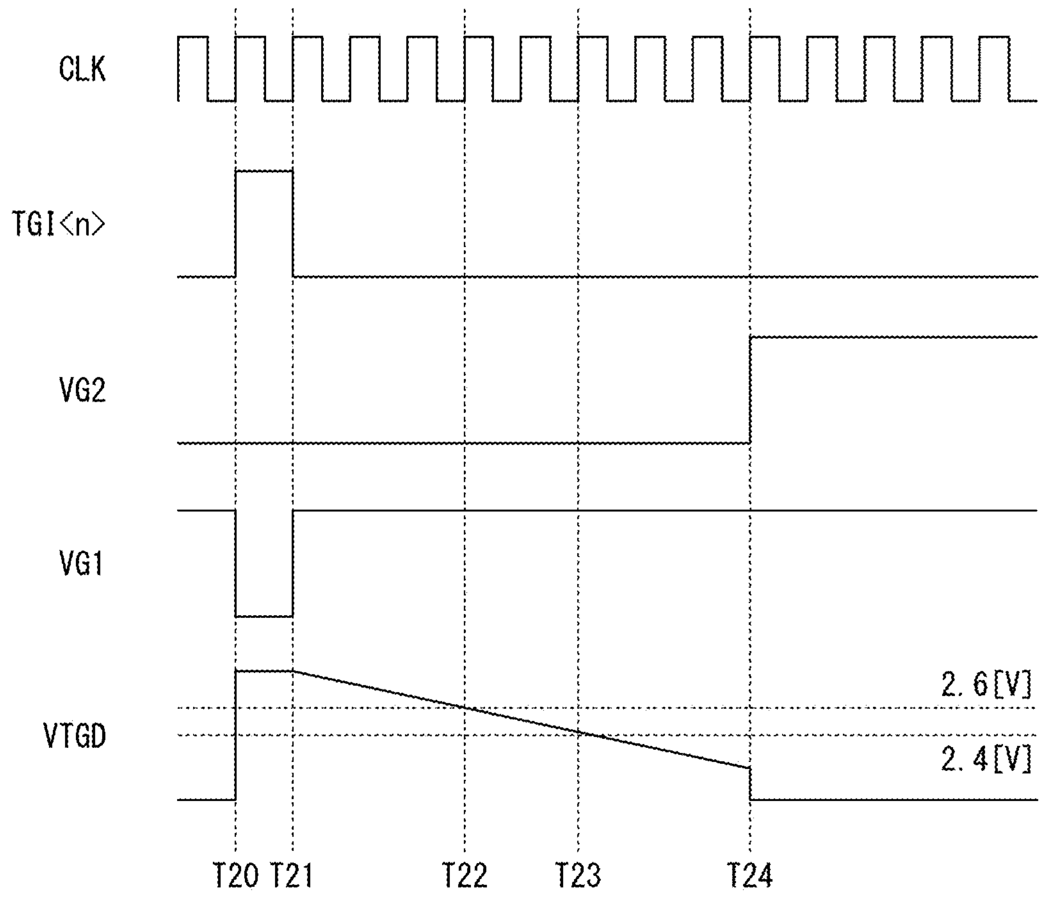
FIG. 10 is a timing chart showing waveforms of signals in the image sensor included in the endoscope system according to the second embodiment of the present invention.

FIG. 10 shows waveforms of the clock signal CLK, the input signal TGI<n>, the transistor control signal VG2, the transistor control signal VG1, and the driving voltage VTGD. The horizontal direction in FIG. 10 indicates time, and the vertical direction in FIG. 10 indicates a voltage value of each signal. An operation of the voltage generation circuit 21*a* will be described by using FIG. 10.

Before a timing T20, the voltage of the input signal TGI<n> is the L voltage. Before the timing T20, the voltage of the transistor control signal VG2 is the L voltage, and the voltage of the transistor control signal VG1 is the H voltage. Therefore, the state of each of the transistor 213 and the transistor 210 is the OFF state. Before the timing T20, the driving voltage VTGD is the same as the reference voltage VSS.

At the timing T20, the voltage of the input signal TGI<n> changes from the L voltage to the H voltage. The voltage of the output signal TGO<n> changes from the L voltage to the H voltage in accordance with the change of the voltage of the input signal TGI<n>. The voltage of the transistor control signal VG1 changes from the H voltage to the L voltage in accordance with the change of the voltage of the output signal TGO<n>. Therefore, the state of the transistor 210 changes from the OFF state to the ON state. At this time, the power source voltage VDD is output from the transistor 210 and is input to the first terminal 212*a* of the capacitor 212. The capacitor 212 holds the power source voltage VDD. The voltage generation circuit 21*a* outputs the same driving voltage VTGD as the power source voltage VDD.

At a timing T21 after the timing T20, the voltage of the input signal TGI<n> changes from the H voltage to the L voltage. The voltage of the output signal TGO<n> changes from the H voltage to the L voltage in accordance with the change of the voltage of the input signal TGI<n>. The voltage of the transistor control signal VG1 changes from the L voltage to the H voltage in accordance with the change of the voltage of the output signal TGO<n>. Therefore, the state of the transistor 210 changes from the ON state to the OFF state.

The current mirror circuit 211 converts the voltage held in the capacitor 212 into the current IS and consumes the electric charge held in the capacitor 212 as the current IS. The voltage of the first terminal 212*a* of the capacitor 212 is output as the driving voltage VTGD. The driving voltage VTGD decreases inversely proportional to time.

In a period from a timing T22 to a timing T23 after the timing T21, the driving voltage VTGD is greater than or equal to 2.4 V and less than or equal to 2.6 V. This period is necessary for driving the transfer transistor 261 of the pixel 26.

At a timing T24 after the timing T23, the voltage of the transistor control signal VG2 changes from the L voltage to the H voltage. Therefore, the state of the transistor 213 changes from the OFF state to the ON state. At this time, the voltage of the first terminal 212*a* of the capacitor 212 is reset to the reference voltage VSS.

Each aspect of the present invention may include the following modified example. The image sensor 10 (imaging device) includes two or more voltage generation circuits 21*a*. The two or more pixels 26 are disposed in a matrix shape including two or more rows and two or more columns.

Each of the two or more voltage generation circuits 21*a* is disposed so as to correspond to any one of the two or more rows.

Each aspect of the present invention may include the following modified example. The vertical selection circuit 22 outputs the output signal TGO<n> for each row of the two or more rows. Each of the two or more voltage generation circuits 21*a* outputs the driving voltage VTGD to a pixel 26 included in the two or more pixels 26 when the output signal TGO<n> output from the vertical selection circuit 22 has been received.

As described above, the voltage generation circuit 21*a* generates the driving voltage VTGD that is lower than the power source voltage VDD and gradually decreases. The voltage generation circuit 21*a* can generate the stable driving voltage VTGD as in the first embodiment.

The two or more voltage generation circuits 21*a* are disposed between the vertical selection circuit 22 and the imaging unit 20. Therefore, delays in the driving voltage VTGD are restricted.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An imaging device configured to operate by using a power source voltage, the imaging device comprising:
- two or more pixels, each of the pixels including:
  - a photoelectric conversion element configured to perform photoelectric conversion and generate an electric charge in accordance with an amount of received light; and
  - a transistor driven by using a driving voltage; and
- a voltage generation circuit configured to generate the driving voltage that is lower than the power source voltage and gradually decreases,
- wherein the voltage generation circuit includes:
  - a capacitor configured to hold a voltage; and
  - a voltage-current conversion circuit configured to convert the voltage held in the capacitor into a current,
- wherein the voltage-current conversion circuit is configured to start conversion into the current after the power source voltage is held in the capacitor, and
- wherein the voltage held in the capacitor gradually decreases and is output as the driving voltage while the voltage-current conversion circuit converts the voltage held in the capacitor into the current.

2. The imaging device according to claim 1,
- wherein the imaging device is driven by using a clock signal, and
- wherein the voltage generation circuit is configured to generate the driving voltage included in a predetermined voltage range from a first timing synchronized with the clock signal to a second timing that is synchronized with the clock signal and is different from the first timing.

3. The imaging device according to claim 1,
- wherein each of the two or more pixels includes a floating diffusion configured to hold the electric charge generated by the photoelectric conversion element, and
- wherein the transistor is configured to transfer the electric charge generated by the photoelectric conversion element to the floating diffusion.

4. The imaging device according to claim 1, comprising two or more of the voltage generation circuits,
- wherein the two or more pixels are disposed in a matrix shape including two or more rows and two or more columns, and
- wherein each of the two or more of the voltage generation circuits is disposed so as to correspond to any one of the two or more rows.

5. The imaging device according to claim 4, comprising a vertical selection circuit configured to output a signal for each row of the two or more rows,
- wherein each of the two or more of the voltage generation circuits is configured to output the driving voltage to a pixel included in the two or more pixels when the signal output from the vertical selection circuit has been received.

6. The imaging device according to claim 4,
- wherein each of the two or more of the voltage generation circuits includes:
  - a capacitor configured to hold a voltage; and
  - a voltage-current conversion circuit configured to convert the voltage held in the capacitor into a current,
- wherein the voltage-current conversion circuit is configured to start conversion into the current after the power source voltage is held in the capacitor, and
- wherein the voltage held in the capacitor gradually decreases and is output as the driving voltage while the voltage-current conversion circuit converts the voltage held in the capacitor into the current.

7. The imaging device according to claim 1,
- wherein the imaging device operates by using a reference voltage lower than the power source voltage, and
- wherein the driving voltage is lower than the power source voltage and is higher than the reference voltage.

8. The imaging device according to claim 1,
- wherein the imaging device operates by using a reference voltage lower than the power source voltage, and
- wherein the driving voltage gradually decreases from a first voltage lower than the power source voltage to a second voltage that is lower than the first voltage and is higher than the reference voltage.

9. An endoscope, comprising:
- a scope to be inserted into a living body; and
- the imaging device according to claim 1,
- wherein the imaging device is disposed in a distal end of the scope.

10. An imaging method using an imaging device that includes two or more pixels and operates by using a power source voltage, the imaging method comprising an imaging step,
- wherein each of the two or more pixels includes:
  - a photoelectric conversion element configured to perform photoelectric conversion and generate an electric charge in accordance with an amount of received light; and
  - a transistor driven by using a driving voltage, and
- wherein the imaging step includes:
  - generating, by using a voltage generation circuit, the driving voltage that is lower than the power source voltage and gradually decreases; and
  - outputting the driving voltage to the transistor,
- wherein the voltage generation circuit includes:
  - a capacitor configured to hold a voltage; and a voltage-current conversion circuit configured to convert the voltage held in the capacitor into a current, wherein the voltage-current conversion circuit is configured to start conversion into the current after the power source voltage is held in the capacitor, and wherein the voltage held in the capacitor gradually decreases and is output as the driving voltage while the voltage-current conversion circuit converts the voltage held in the capacitor into the current.

11. An imaging device configured to operate by using a power source voltage, the imaging device comprising:

two or more pixels, each of the pixels including:

a photoelectric conversion element configured to perform photoelectric conversion and generate an electric charge in accordance with an amount of received light; and a transistor driven by using a driving voltage; and two or more voltage generation circuits, each of the voltage generation circuits being configured to generate the driving voltage that is lower than the power source voltage and gradually decreases, wherein the two or more pixels are disposed in a matrix shape including two or more rows and two or more columns, wherein each of the two or more voltage generation circuits is disposed so as to correspond to any one of the two or more rows, wherein the imaging device comprises a vertical selection circuit configured to output a signal for each row of the two or more rows, and wherein each of the two or more voltage generation circuits is configured to output the driving voltage to a pixel included in the two or more pixels when the signal output from the vertical selection circuit has been received.

* * * * *